United States Patent
Tang et al.

(10) Patent No.: US 7,335,185 B2
(45) Date of Patent: Feb. 26, 2008

(54) PROTECTIVE COATINGS FOR MEDICAL DEVICES

(75) Inventors: Nie Tang, Maple Grove, MN (US); Daniel Horn, Shoreview, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 689 days.

(21) Appl. No.: 10/622,624

(22) Filed: Jul. 18, 2003

(65) Prior Publication Data

US 2005/0015105 A1    Jan. 20, 2005

(51) Int. Cl.
*A61M 29/00*    (2006.01)
(52) U.S. Cl. .............................................. 604/103.11
(58) Field of Classification Search ........... 604/103.08, 604/103.05, 101.01, 101.06, 103.11, 103.07, 604/103.12; 606/192, 194; 623/1.11, 1.12
See application file for complete search history.

(56) References Cited

U.S. PATENT DOCUMENTS

| | | | |
|---|---|---|---|
| 4,948,628 A | 8/1990 | Montgomery et al. | 427/570 |
| 5,451,428 A | 9/1995 | Rupp | 427/2.12 |
| 5,576,072 A | 11/1996 | Hostettler et al. | 427/532 |
| 5,662,960 A | 9/1997 | Hostettler et al. | 427/2.3 |
| 5,804,263 A | 9/1998 | Goldberg et al. | 428/34.7 |
| 5,849,368 A | 12/1998 | Hostettler et al. | 427/536 |
| 5,919,570 A | 7/1999 | Hostettler et al. | 428/424.8 |
| 5,932,299 A | 8/1999 | Katoot | 427/508 |
| 6,017,577 A | 1/2000 | Hostettler et al. | 427/2.12 |
| 6,030,656 A | 2/2000 | Hostettler et al. | 427/2.3 |
| 6,040,058 A | 3/2000 | Hostettler et al. | 428/457 |
| 6,063,318 A | 5/2000 | Houser et al. | 264/248 |
| 6,080,488 A | 6/2000 | Hostettler et al. | 428/423.3 |
| 6,120,904 A | 9/2000 | Hostettler et al. | 428/423.3 |
| 6,174,329 B1 | 1/2001 | Callol et al. | 623/1.34 |
| 6,265,016 B1 | 7/2001 | Hostettler et al. | 427/2.11 |
| 6,287,277 B1 | 9/2001 | Yan | 604/96.01 |
| 6,299,596 B1 | 10/2001 | Ding | 604/96.01 |
| 6,462,012 B1 | 10/2002 | Wevers et al. | 510/441 |
| 6,468,304 B1 | 10/2002 | Dubois-Rande et al. | 623/1.42 |
| 6,495,624 B1 | 12/2002 | Brown | 524/462 |
| 6,939,321 B2 * | 9/2005 | Wang et al. | 604/103.08 |
| 6,946,173 B2 * | 9/2005 | Lim et al. | 604/103.08 |
| 2002/0009604 A1 | 1/2002 | Zamora et al. | 428/450 |
| 2002/0037358 A1 | 3/2002 | Barry et al. | 427/2.1 |
| 2002/0054900 A1 | 5/2002 | Kamath et al. | 424/425 |
| 2002/0111590 A1 | 8/2002 | Davila et al. | 604/265 |
| 2002/0114954 A1 | 8/2002 | Badyal et al. | 428/422 |
| 2002/0146557 A1 | 10/2002 | Claude et al. | 428/336 |
| 2002/0165523 A1 | 11/2002 | Chin et al. | 604/523 |

* cited by examiner

*Primary Examiner*—Kevin T. Truong
(74) *Attorney, Agent, or Firm*—Vidas, Arrett & Steinkraus, P.A.

(57) ABSTRACT

A dilatation balloon formed of a first material and further including at least one first plasma polymerized layer which forms the top most surface of the balloon, and a method of making the same.

23 Claims, 2 Drawing Sheets

PROTECTIVE COATINGS FOR MEDICAL DEVICES

FIELD OF THE INVENTION

The present invention relates to coatings for medical devices and to methods of making and using the same.

BACKGROUND OF THE INVENTION

Balloon catheters are well-known devices in which the catheter carries an inflatable balloon to occlude and seal a body space, to expand a blood vessel through pressurized inflation of the balloon, or for any other desired purpose which may typically but not necessarily be a therapeutic purpose in the medical field. In the case of dilatation balloon catheters for angioplasty, for example a PTCA procedure, the catheter balloon is commonly made out of a thin, strong material which is of relatively low resilience. Examples of materials from which a catheter balloon may be made include biaxially oriented polyethylene terephthalate (PET) copolymers, a polyamide material such as nylon or polyether-block-amide copolymers to mention only a few. These materials are typically strong, flexible materials and have the advantage that they are flexible but inelastic so that they can expand outwardly to a predetermined diameter, and then cease further expansion at normal pressures, to avoid damage to the artery wall by over expansion.

The fact that balloon angioplasty requires extremely thin walled material, high strength (i.e. high tensile), relatively inelastic material of predictable inflation properties, leads to a common problem which is that the balloons can be easily punctured through abrasion or the like, even though they have a high tensile strength. Pin holes and ruptures are a fairly common problem when such catheter balloons are used in contact with rough surfaces. Also, tiny flaws in the mold of such balloons can create weak spots, since the balloons are so thin-walled. However, it is impractical to increase the wall thickness of these balloons because then they become too stiff, with high flexural moduli, with the result that such balloons do not collapse properly on deflation to facilitate easy withdrawal from the vascular system of a patient.

Further, thin walls are necessary because the balloon's wall and waist thicknesses limit the minimum diameter of the distal end of the catheter and therefore determine the limits on vessel size treatable by the method and the ease of passage of the catheter through the vascular system. High strength is necessary because the balloon is used to push open a stenosis and so the thin wall must not burst under the high internal pressures necessary to accomplish this task. The balloon must have some elasticity so that the inflated diameter can be controlled, so as to allow the surgeon to vary the balloon's diameter as required to treat individual lesions, but that elasticity must be relatively low so that the diameter is easily controllable. Small variations in pressure must not cause wide variation in diameter.

The high strength biaxially oriented polyethylene terephthalate (PET) or polyamides such as nylon or the polyamide copolymers tend to be less elastic, and have less resilience. Balloon catheters may be made of more elastic materials such as polyolefins or polyolefin copolymers, but typically, in order to achieve the high tensile strength, the balloon walls must be made thicker.

Coatings may be used to modify the surface of the balloon to improve abrasion and puncture resistance, but such coatings typically increase the wall thickness, and decrease the flexibility and thus increase the stiffness and flexural moduli of the balloon. This increased stiffness and increased flexural moduli can result in balloons which do not collapse properly on deflation to facilitate easy withdrawal from the vascular system of a patient.

Coatings may be used for other purposes such as increasing lubricity as well and for delivering therapeutic agent(s), for example. Typically, such coatings are provided by dipping, brushing, painting, and so forth.

U.S. Pat. No. 6,287,277 describes balloons formed by a vacuum deposition process.

U.S. Pat. No. 5,451,428 describes a plasma polymerizing an intermediate layer onto a medical device which is then used to react with a biocompatible coating to provide optimum adhesion of the biological coating.

There remains a need for materials and methods which can provide improved balloon catheters which are thin walled, yet have a durable, abrasion and tear resistant surface thereby improving the resistance to pinhole formation, and yet are relatively flexible, yet inelastic to allow the balloons to expand outwardly to a predetermined diameter, and then cease further expansion at normal pressures, to avoid damage to the artery wall by overexpansion.

SUMMARY OF THE INVENTION

In one aspect, the present invention relates to implantable medical devices having proximal and distal ends adapted for manipulation outside of the body. The device includes an elongate body extending between the proximal and distal ends and a polymeric expandable portion located at the distal end of the elongate body. The expandable portion further includes at least one first plasma polymerized layer which forms the outer most layer of the expandable portion. The expandable portion may be a dilatation balloon, such as those used for angioplasty. In some embodiments, more than one plasma polymerized layer is employed.

The plasma polymerized layer(s) is formed through the use of monomers in gaseous form and which when exposed to a source of electromagnetic radiation which irradiates high frequency waves, undergo plasma polymerization. The "plasma" is a partially ionized gas in which highly reactive free radicals and/or ions are present. The gaseous monomers condense and crosslink on the surface of the medical device. The crosslink density can be controlled by the amount of monomer supplied, as well as the conditions under which the plasma polymerization is conducted.

The present invention finds utility for providing a protective layer on the surface of a balloon.

The present invention has found that certain plasma polymerized coatings provide improved abrasion resistance.

The present invention further relates to a method of coating the surface of a catheter balloon with an abrasion resistant coating. The method includes the steps of exposing the balloon to at least one first gaseous monomer composition and exposing the gaseous monomer to electromagnetic waves to form a plasma. The monomers condense on the surface of the catheter balloon and crosslink to form at least one first plasma polymerized layer on the surface of the balloon. The first plasma polymerized layer forms the outermost layer of the catheter balloon.

A second plasma polymerized layer can also be applied to the surface of the balloon in the same manner. The second layer is applied between the first plasma polymerized layer and the catheter balloon. In one embodiment, the second layer is an abrasion resistant coating, and the first plasma polymerized layer is a softer coating.

DETAILED DESCRIPTIONS OF THE PREFERRED EMBODIMENTS

While this invention may be embodied in many different forms, there are described in detail herein specific embodiments of the invention. This description is an exemplification of the principles of the invention and is not intended to limit the invention to the particular embodiments illustrated.

Figure 1:
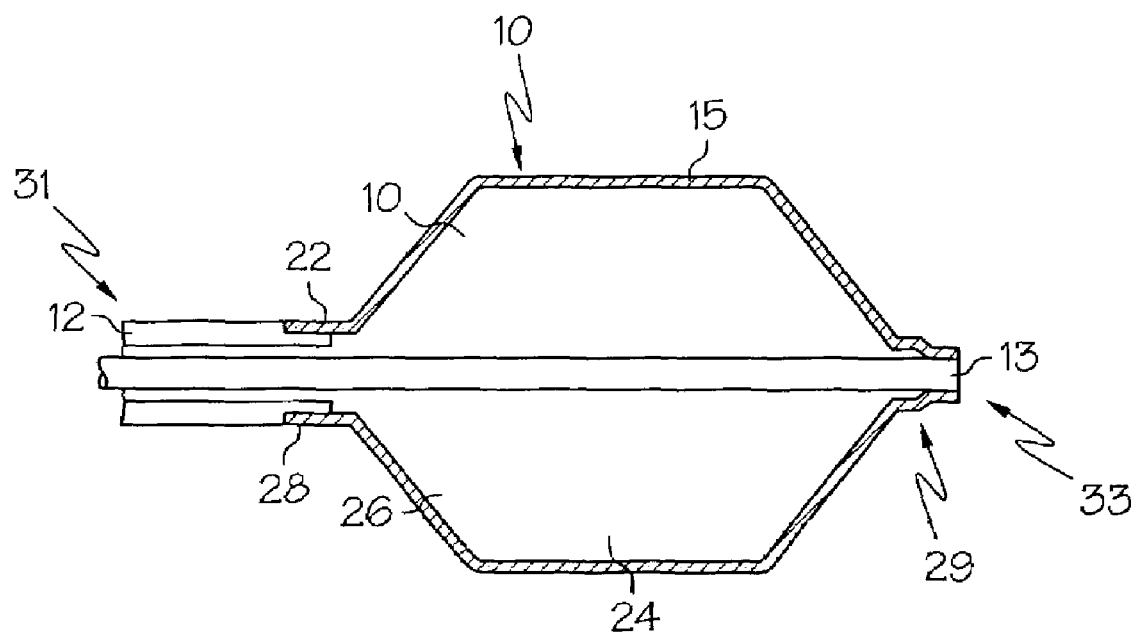
FIG. 1 is a cross sectional view of a balloon having at least one plasma polymerized layer according to the present invention.

Turning first to the figures, FIG. 1 illustrates generally at 10, a dilatation balloon according to the invention shown in an inflated state. It should be noted that in each of the following figures, lines and dimensions are not shown to scale. Such figures are for illustrative purposes only. Balloon 10 has a body 24, cones 26 and waist portions 22. In this particular embodiment, proximal end 28 of balloon 10 is shown secured by adhesively bonding, welding or some such method to the distal outer tube 12 and the distal end 29 of balloon 10 is shown secured to the distal end of inner tube 13. The balloon in this embodiment is shown with a single plasma polymerized layer 15 of a material which improves abrasion and puncture resistance of the balloon.

One of ordinary skill in the art would understand that there are numerous other balloon configurations and that the present invention is not limited to any one particular configuration. These figures are for illustrative purposes only.

Figure 2:
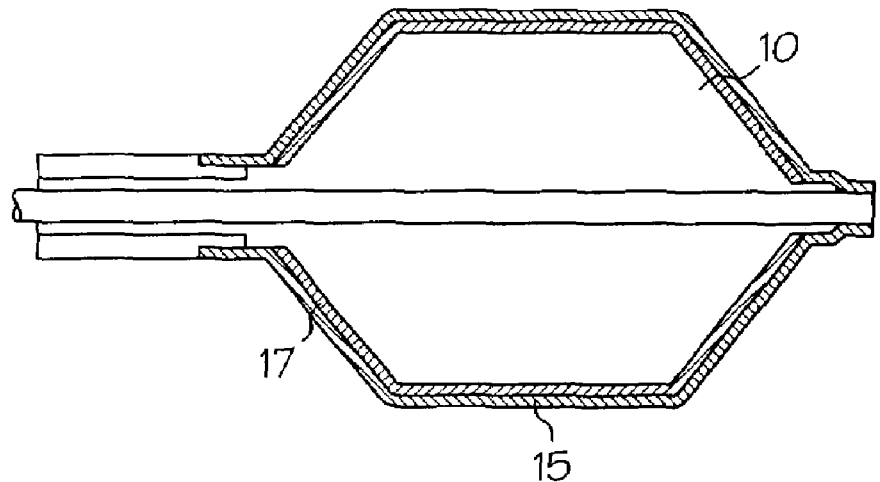
FIG. 2 is a cross sectional view of a balloon according to the present invention which has more than one plasma polymerized layer.

FIG. 2 is a cross sectional view of the same type of balloon structure as shown in FIG. 1. However, in this embodiment, balloon 10 is further shown with a second plasma polymerized layer 17 located between the balloon 10 and the first plasma polymerized layer 15. In this embodiment, the second plasma polymerized layer 17 is such that it provides the balloon with abrasion and puncture resistance and the first outer plasma polymerized layer 15 is such as to provide a better surface for the stent to grip. Thus, the first outer plasma polymerized layer 15 is relatively softer than the second intermediate plasma polymerized layer 17.

Figure 3:
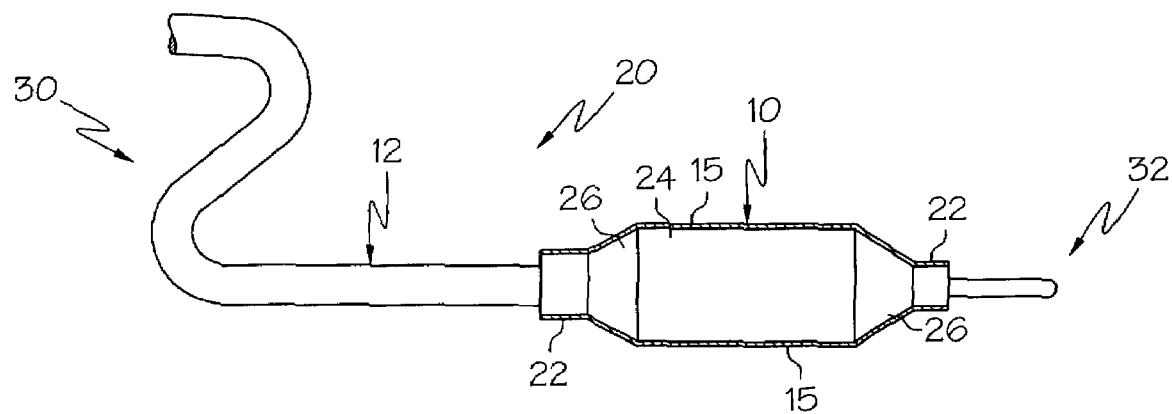
FIG. 3 is a side view of a balloon according to the present invention which has at least one plasma polymerized layer in combination with a catheter device.

FIG. 3 illustrates a balloon catheter 20 according to the present invention having an elongated flexible shaft 12 and an inflatable balloon 10. Catheter 20 has a proximal end 30 and a distal end 32. Inflatable balloon 10 is mounted at the distal end 32 of the elongated flexible shaft 12. Except as noted herein, catheter 20 is conventional in its construction, providing a lumen communicating with the interior of balloon 10, for inflation and deflation of the balloon, and other optional features conventional in the dilatation catheter art. The balloon 10 is shown in an inflated configuration and has a body 24, cones 26 and waist portions 22. The balloon is shown with a single plasma polymerized layer 15 on the body 24, cones 26 and waist portions 22. Balloon may optionally have more plasma polymerized layers as well. In this embodiment, the single plasma polymerized layer provides a hard abrasion resistant coating. During a medical procedure, proximal end 30 remains outside of the patient's body and typically has a means for manipulating the distal end 32 of the device from outside of the body (not shown).

Figure 4:
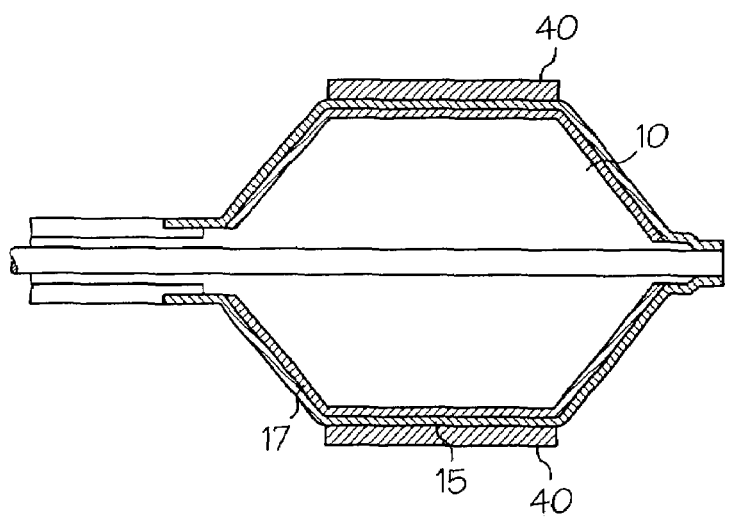
FIG. 4 is a side view of a balloon according to the present invention which has more than one plasma polymerized layer in combination with a stent.

FIG. 4 is a cross sectional view of the same balloon shown in FIG. 3 in combination with a stent 40.

The coatings according to the present invention are applied to the balloon using a technique known as plasma polymerization. The balloon on which the plasma is to be deposited is placed in a plasma deposition chamber with a vacuum. Suitably, the deposition chamber is pressure tight, and a pressure below atmospheric is applied such that the chamber substantially forms a vacuum within. Typical pressures are between about $10^{-5}$ bar to $10^{-2}$ bar. Chambers for plasma polymerization are known in the art. Monomers in gaseous form are then conducted into the chamber. A source of energy, i.e. electromagnetic radiation irradiates high-frequency waves into the chamber, thereby creating a plasma.

Plasma polymerization is initiated through the use of a non-equilibrium ionized gas plasma. The "plasma" is a partially ionized gas in which free radicals and/or ions are present. Whereas a free radical is a highly reactive chemical species carrying no charge and having a single unpaired electron in an orbital, a cation is a positively charged ion or an atom or group of atoms that has lost one or more electrons and an anion is a negatively charged ion or an atom or group of atoms that has gained one or more electrons.

The majority of polymerization, however, is completed in the absence of the plasma. Gaseous monomers condense on the article, i.e. the balloon, as highly cross-linked layers. In this manner, a high molecular weight polymer may be formed.

The formation of the ionized gas plasma may be accomplished by any of the techniques known to produce such plasmas. For example, see J. R. Hollahan and A. T. Bell, eds., "Techniques in Applications of Plasma Chemistry", Wiley, New York, 1974 and M Shen, ed. "Plasma Chemistry of Polymers", Marcel Dekker, New York, 1976. For example, using one method, an ionizable gas is contained under vacuum between parallel plate electrodes connected to a radio frequency generator. The plasma can be created with parallel plates that are either external or internal to the plasma deposition chamber. Other methods include use of an external induction coil to create an electric field which produces the plasma of ionized gas, or use of oppositely charged electrode points placed directly into the plasma vacuum chamber in spaced apart relationship to create the plasma. See also U.S. Pat. No. 6,462,012, the entire content of which is incorporated by reference herein.

The present inventors have found that the amount of crosslinking density can be controlled, and thus the physical properties of the plasma polymerized layer by altering plasma process conditions such as power, vacuum and flow rate, as well as the type of monomers used in the process. In this manner, the hardness of the coating can be manipulated to achieve improvements in balloon durability as well as stent retention. For example, a harder coating with improved durability may be obtained by higher power input and lower flow rate, and a soften coating for better stent retention may be obtained by lower power and higher flow rate.

Another technique which may be employed to obtain a softer outer layer is through the use of plasma enhanced polymerization. Using this technique, conventional polymerization reactions are initiated and propagated and polymers with structures similar to those of the monomer can be obtained.

In one embodiment, a multi-layered balloon is obtained having a mid-layer with a harder coating for improved durability, with an outer layer which is softer for better stent retention.

Stent securement is a key consideration. Balloons having a thin-walled, small diameter design, typically have a thinner wall thickness and increased risk of burst failure. The plasma polymerized layer with high crosslink density can provide a strong, durable coating, without dramatically increasing the wall thickness and balloon diameter.

To apply the polymer coating, the medical device is put in a closed, preferably pressure-tight chamber. Any chamber used for such reactions can be employed in the present invention. The chamber may be of any configuration including, for example, bell shaped, cubic, rectangular, or any other shape typical to vacuum chambers. The chamber can also be formed of a variety of materials including, for example, steel, glass, polymers, ceramic or composites.

The monomers in gas form are streamed through a valve or other appropriate opening, into the deposition chamber. A source or radiant energy is applied to the chamber. Any suitable configuration for application of the energy to the chamber may be employed. Electromagnetic waves irradiated into the chamber and the spark discharge causes the gas to form a plasma which is a gas having free radicals or ions, i.e. anions or cations. Frequencies which may be employed include, for example, alternating current (AC) of about 50-60 Hz, radio frequency (RF) of about 13.56 MHz or microwave frequency of about 2.45 GHz.

The method according to the present invention allows a very thin plasma polymerized film to be laid down on the surface of the balloon, thereby keeping the increase in wall thickness of the balloon to a minimum. In fact, plasma polymerization as employed herein can be used to form a layer of high crosslink density which is similar to a monolayer, being as little as about 100-2000 Å thick, more typically about 300-2000 Å, and even more suitably about 1000-2000 Å.

The method according to the present invention can also be employed to put down multiple layers having different properties such as those going from hard to soft. The hardness/softness of the plasma polymerized layer can be controlled by the amount of polymerization or crosslink density. This in turn is controlled by the type of monomer, and the power, vacuum and flow rate employed in the process.

Any monomer capable of forming a plasma which has free radicals and/or ions, i.e. cations or anions, when subjected to electromagnetic radiation may be employed herein. More specifically, examples of monomers useful in forming the plasma polymerized layer as described herein include, but are not limited to hydrocarbons, nitrogen containing compounds, fluorine containing monomers, silicon containing monomers, oxygen containing monomers, and mixtures thereof.

Some examples of suitable hydrocarbons includes those having reactive double bonds and triple bonds, aromatic compounds, and so forth.

More specific examples of suitable hydrocarbons include, but are not limited to, methane, ethylene, propylene, butadiene, benzene, xylene, toluene, mixtures thereof, and so forth.

Examples of suitable nitrogen containing compounds include the amines and the nitriles. Examples of suitable amines include, for example, pyrrole, a cyclic, secondary amine structure.

Examples of suitable fluorocarbons include, but are not limited to, fluoroalkyls, perfluoroalkyls such as perfluoropropane and perfluoroalkenes such as perfluorobutene, fluorohydroalkyls, cyclofluoroalkyls, fluorobenzene, and so forth. The advantage of employing fluorocarbons is that the lubricity of the balloon surface as well as abrasion and puncture resistance, can also be increased. Use of fluorinated monomers for plasma polymerization are described in U.S. Pat. No. 6,495,624 which is incorporated by reference herein in its entirety.

Examples of suitable oxygen containing compounds include, but are not limited to, ethers, esters and acids.

Examples of suitable silicon containing compounds include silanes, siloxanes, silazenes, and so on and so forth. Specific examples of suitable silanes include, but are not limited to, dimethylsilane, trimethylsilane, aminopropyltriethoxysilane, and so forth.

Specific examples of suitable siloxanes include, but are not limited to, dimethylsiloxane, trimethylsiloxane, and so forth.

Members of the titanate family may also be employed in the plasma polymerization process described herein.

Monomers having ethylenic unsaturation such as vinyl monomers, may also be employed in the present invention. Examples of monomers having ethylenic unsaturation include, but are not limited to, N-vinylpyrrolidone (NVP), hydroxyethylmethacrylate (HEMA), vinyl substituted polyethers such as vinyl-polyethylene glycol (VPEG) or vinyl-polypropylene glycol (VPPG), acrylamide (AM), dimethylacrylamide (DMA), hydroxy-propylacrylates, and so forth.

Of course, mixtures of any of the above materials may also be employed.

The balloon may be formed from any suitable material known in the art. Examples of suitable balloon materials include, but are not limited to, polyesters and copolymers thereof such as polyethylene and copolymers thereof, polyesters and copolymers thereof such as polyethylene terephthalate (PET), polyamides such as nylon and SELAR® and copolymers thereof such as polyether-block-amides (PEBAX®), elastomeric polyesters and copolymers thereof such as HYTREL® polyetheroester, and so forth.

The balloon is placed in a high pressure deposition chamber, the appropriate monomers in gaseous form are conducted into the chamber, and the chamber is then exposed to electromagnetic radiation. The source of the electromagnetic ratio may be direct current, alternating current, microwave, radio-frequency plasma, electron beam, gamma radiation, and so forth. The monomers condense and crosslink on the surface of the balloon. The amount of deposition as well as the crosslink density, can be controlled by deposition time, sample location, power, and flow rate.

The resultant crosslinked plasma coating has excellent adhesion to the balloon surface, and provide a thin, very strong, chemically resistant permanent coating. The coating can be advantageously used to increase the surface hardness of the balloon, thereby improving abrasion resistance, and decreases pinhole formation, leakages and ruptures.

Because the coating can be deposited as a very think layer, i.e. about 1000-2000 Å, it has no negative impact on balloon profile.

The following non-limiting examples further illustrate embodiments of the present invention.

EXAMPLES

Test Methods

1. Abrasion Testing

Balloon ends were attached to a fixture which can slide back and forth. The center portion of the balloons were located such that it rested on top of a diamond tipped file. The balloons were inflated to 88 psi (about 91 kg/cm$^2$). A load was selected and placed on the balloons which can be varied between 1 and 2000 grams. The balloons were dragged across the file surface and observed for bursting or leaking.

Example 1

The effects of the plasma coatings on balloon performance was evaluated using abrasion testing.

Coated balloons were compared to non-coated (control) balloons. The monomer employed was pyrrole. The base control balloons employed had a diameter of 3.0 mm and are described in the following table 1.

TABLE 1

| Control Balloon | Material | 2x Wall Thickness (in) | 2x Wall Thickness Std. Dev. |
|---|---|---|---|
| A | PEBAX 7233 | 0.00122 (0.00309 cm) | 3.162E−05 |
| B | PEBAX 7233 | 0.00109 (0.00276 cm) | 1.789E−05 |

The balloons were coated using five different plasma coating conditions. The groups each included both A balloons coated with a plasma polymerized layer and B balloons coated with a plasma polymerized layer described in Table 1 above. The conditions employed for each group are shown in the following Table 2.

TABLE 2

| Identifier | Balloon | Monomer | Coating Time | Pre-cleaning | Power (W)/ Pressure (mTorr) | Coating Successful? |
|---|---|---|---|---|---|---|
| Group 1 | B | Pyrrole | 3 min | 10 min Argon | 80/150 | Yes |
| Group 2 | B | Pyrrole | 5 min | 10 min Argon | 80/275 | Yes, but not uniform |
| Group 3 | A | Pyrrole | 1 min | 5 min Oxygen | 80/250 | Yes |
| Group 4 | A | Pyrrole | 3 min | 5 min Oxygen | 60/250 | Yes |
| Group 5 | A | Pyrrole | 5 min | 5 min Oxygen | 60/250 | Yes |
| A | | none | — | — | — | — |
| B | | none | — | — | — | — |

After plasma coating, the balloons were subjected to abrasion testing with the results shown in the following Table 3.

TABLE 3

Abrasion Test Summary

| Identifier | Load (g) | Total No. Tested | Failed | Did not Fail |
|---|---|---|---|---|
| Group 1 | 200 | 5 | 5 | 0 |
| Group 2 | 200 | 7 | 3 | 4 |
| Group 3 | 250 | 7 | 5 | 2 |
| Group 4 | 250 | 7 | 3 | 4 |
| Group 5 | 250 | 7 | 0 | 7 |
| Group 5 | 300 | 1 | 0 | 1 |
| Group 5 | 400 | 1 | 0 | 1 |
| Group 5 | 500 | 1 | 1 | 0 |
| A | 250 | 7 | 6 | 1 |
| A | 200 | 1 | 1 | 0 |
| A | 150 | 1 | 1 | 0 |
| A | 100 | 1 | 1 | 0 |
| A | 50 | 1 | 0 | 1 |
| B | 200 | 7 | 7 | 0 |
| B | 150 | 1 | 1 | 0 |
| B | 100 | 1 | 1 | 0 |
| B | 50 | 1 | 1 | 0 |
| B | 10 | 1 | 1 | 0 |
| B | 5 | 1 | 1 | 0 |
| B | 2 | 1 | 1 | 0 |
| B | 1 | 1 | 0 | 1 |

Both balloon bursts as well as leaks were indicated as a failure. The load was increased many times for the group 5 samples to find out the point at which failures would occur. Additional samples were also tested for the A group and the B group in order to discover at which load these balloons exhibited failures. An inspection of the group 2 balloons showed that the coating was non-uniform indicating why some samples failed while others in the group did not.

The above disclosure is intended to be illustrative and not exhaustive. The description will suggest many variations and alternatives to those of ordinary skill in the art. All of these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A dilatation balloon formed from a first material and further comprising at least one first plasma polymerized layer which forms the outer most layer of said balloon.

2. The balloon of claim 1 wherein said plasma polymerized layer is formed by the reaction of a monomer selected from the group consisting of hydrocarbons, amines, nitriles, fluorocarbons, silanes, siloxanes, silazenes, titanates, ethers, esters, acids, alcohols and mixtures thereof.

3. The balloon of claim 1 wherein said at least one plasma polymerized layer is formed using at least one organic monomer.

4. The balloon of claim 2 wherein said hydrocarbon is methane, ethylene, propylene, butadiene, benzene, toluene, xylene and mixtures thereof.

5. The balloon of claim 1 wherein said at least one plasma polymerized layer is formed by at least one pyrrole monomer.

6. The balloon of claim 1 wherein said monomer is a fluorocarbon selected from the group consisting of fluoroalkyls, fluorohydroalkyls, cyclofluoroalkyls, fluorobenzene and mixtures thereof.

7. The balloon of claim 1 further comprising a second plasma polymerized layer which is between said balloon and said at least one first plasma polymerized layer.

8. The balloon of claim 7 wherein said second plasma polymerized layer is harder than said at least one first plasma polymerized layer.

9. An implantable medical device having proximal and distal ends adapted for manipulation outside of the body said device comprising:
   a polymeric elongate body extending between proximal and distal ends of said device; and
   a polymeric expandable portion located at said distal end of said elongate body;
   wherein said expandable portion comprising at least one first plasma polymerized layer which forms the outer most layer of the expandable portion.

10. The medical device of claim 9 wherein said expandable portion is a dilatation balloon.

11. The medical device of claim 10 wherein said balloon is a multilayer balloon comprising at least one second plasma polymerized layer which forms an intermediate layer between said balloon and said first plasma polymerized layer, said first plasma polymerized layer is softer than said second plasma polymerized layer.

12. The medical device of claim 11 wherein said intermediate layer is formed through the reaction of pyrrole monomer.

13. The medical device of claim 10 further comprising a stent disposed about said dilatation balloon.

14. A method of coating the surface of a catheter balloon with an abrasion resistant coating said method comprising the steps of:
   (a) exposing said balloon to at least one first gaseous monomer composition; and
   (b) exposing said gaseous monomer to electromagnetic waves to form a plasma said monomers condensing on said catheter balloon and crossliniking to form at least one first plasma polymerized layer, and
   wherein said at least one first plasma polymerized layer forms the outermost layer of said catheter balloon.

15. The method of claim 14 wherein said monomer is selected from the group consisting of hydrocarbon monomers, silicon containing monomers, fluorocarbon monomers, ethylenically unsaturated monomers, titanates, and mixtures thereof.

16. The method of claim 15 wherein said monomer is a hydrocarbon monomer selected from the group consisting of benzene, toluene, xylene, methane, ethylene, propylene, butadiene and mixtures thereof.

17. The method of claim 15 wherein said monomer is a fluorocarbon selected from the group consisting of fluoroalkyls, fluorohydroalkyls, cyclofluoroalkyls, fluorobenzene and mixtures thereof.

18. The method of claim 14 wherein said monomer is pyrrole.

19. The method of claim 14 wherein said monomer is an organic monomer.

20. The method of claim 14 further comprising the steps of:
   c) exposing said balloon to at least one second gaseous monomer composition; and
   d) exposing said at least one second gaseous monomer composition to electromagnetic waves to form a plasma said monomers condensing on said catheter balloon and crossliniking to form at least one first plasma polymerized layer, and
   wherein steps c) and d) occur before steps a) and b) and wherein said at least one first plasma polymerized layer forms the outermost layer of said catheter balloon.

21. The method of claim 20 wherein said second plasma polymerized layer is harder than said first plasma polymerized layer.

22. The dilatation balloon of claim 1 wherein said at least one first plasma polymerized layer has a thickness of about 100-2000 Å thick.

23. The balloon of claim 1 wherein said balloon is formed from polyether-block-amide and said first plasma-polymerized layer comprises pyrrole.

* * * * *